US010920154B2

(12) United States Patent
Anderson et al.

(10) Patent No.: US 10,920,154 B2
(45) Date of Patent: Feb. 16, 2021

(54) PROCESS FOR DESALTING CRUDE OIL (71) Applicant: Petroliam Nasional Berhad (Petronas), Kuala Lumpur (MY)

(72) Inventors: Kris Anderson, Kuala Lumpur (MY); Azlan Hussain, Kuala Lumpur (MY); Martin Atkins, Kuala Lumpur (MY); Jamali Basar, Kuala Lumpur (MY)

(73) Assignee: Petroliam Nasional Berhad (Petronas), Kuala Lumpur (MY)

( * ) Notice: Subject to any disclaimer, the term of this patent is extended or adjusted under 35 U.S.C. 154(b) by 600 days.

(21) Appl. No.: 14/414,766

(22) PCT Filed: Jul. 26, 2013

(86) PCT No.: PCT/EP2013/065846
§ 371 (c)(1),
(2) Date: Jan. 14, 2015

(87) PCT Pub. No.: WO2014/016425
PCT Pub. Date: Jan. 30, 2014

(65) Prior Publication Data
US 2015/0191659 A1  Jul. 9, 2015

(30) Foreign Application Priority Data
Jul. 27, 2012  (MY) .............. PI2012003403

(51) Int. Cl.
*B01D 17/06*  (2006.01)
*B03C 11/00*  (2006.01)
(Continued)

(52) U.S. Cl.
CPC ............. *C10G 21/08* (2013.01); *B01D 17/06* (2013.01); *B03C 11/00* (2013.01); *C07C 51/48* (2013.01);
(Continued)

(58) Field of Classification Search
CPC ........ C10G 21/08; C10G 21/28; C10G 31/08; C10G 33/00; C10G 53/02; C10G 27/12;
(Continued)

(56) References Cited

U.S. PATENT DOCUMENTS 4,684,457 A * 8/1987 McKechnie .......... C10G 31/08
208/187
4,806,231 A * 2/1989 Chirinos ................ C10G 31/08
208/187
(Continued)

FOREIGN PATENT DOCUMENTS

EP       0881274      12/1998
WO     WO9950375     10/1999
(Continued)

OTHER PUBLICATIONS

Genesis Group, "Crude Oil". Accessed May 9, 2019.*
International Search Report dated Oct. 11, 2013.

*Primary Examiner* — Benjamin L Lebron
(74) *Attorney, Agent, or Firm* — Ryan T. Grace; Advent, LLP (57) ABSTRACT The present invention relates to a process of desalting crudeoil, in particular a process for desalting a crude oil which comprises an ionic liquid, an organic acid and any resulting organic salt.

24 Claims, 6 Drawing Sheets (51) Int. Cl.
*C07C 51/48* (2006.01)
*C10G 21/08* (2006.01)
*C10G 21/28* (2006.01)
*C10G 31/08* (2006.01)
*C10G 33/00* (2006.01)
*C10G 53/02* (2006.01)
*C10G 33/02* (2006.01)
*B01D 17/04* (2006.01)

(52) U.S. Cl.
CPC ............. *C10G 21/28* (2013.01); *C10G 31/08* (2013.01); *C10G 33/00* (2013.01); *C10G 33/02* (2013.01); *C10G 53/02* (2013.01); *B01D 17/045* (2013.01); *C10G 2300/1033* (2013.01)

(58) Field of Classification Search
CPC ........ C10G 27/00; C10G 29/06; C10G 29/12; C10G 29/20; C10G 53/14; C10G 2300/1033; C10G 2300/308; C10G 2300/805; C10G 2300/205; C10G 33/02; C02F 1/722; C02F 1/683; C02F 2103/10; C07C 51/48; B01D 17/045; B01D 17/06; B03C 11/00

See application file for complete search history.

(56) References Cited

U.S. PATENT DOCUMENTS

| | | | |
|---|---|---|---|
| 2003/0188995 A1* | 10/2003 | Varadaraj | C10G 31/08 208/251 R |
| 2004/0167233 A1* | 8/2004 | Varadaraj | B01D 17/00 516/197 |
| 2007/0298505 A1* | 12/2007 | Smith | B01J 45/00 436/61 |
| 2008/0156649 A1* | 7/2008 | Sams | B01D 17/00 204/554 |
| 2010/0234247 A1 | 9/2010 | Varadaraj et al. | |
| 2010/0256020 A1* | 10/2010 | Aston | C09K 8/035 507/130 |
| 2011/0155647 A1 | 6/2011 | Serban et al. | |
| 2011/0186515 A1 | 8/2011 | Guimaraes et al. | |
| 2012/0125818 A1 | 5/2012 | O'Rear et al. | |
| 2014/0091008 A1* | 4/2014 | Hardacre | C10G 19/02 208/14 |

FOREIGN PATENT DOCUMENTS

| | | | | |
|---|---|---|---|---|
| WO | WO 2010136783 A1 * | 12/2010 | | C10G 21/27 |
| WO | 2012069832 A2 | 5/2012 | | |

* cited by examiner

PROCESS FOR DESALTING CRUDE OIL

The present invention relates to a process of desalting crude oil, in particular a process for desalting a crude oil which comprises an ionic liquid, an organic acid and any resulting organic salt.

Desalters have been used for many years for removing inorganic salts from crude oil. Typical desalters comprise a tank into which crude oil and water are added. The salts from the crude oil are extracted via the aqueous phase. In typical desalting processes, water is only introduced into the tank in a small amount. This is to maximise the quantity of crude oil that can be treated and to minimise the quantity of waste water that will be sent to the effluent treatment facility. A small amount of water also minimises the amount of corrosion and fouling that occurs in a desalting apparatus. For instance, crude oil typically contains small inorganic salts, such as NaCl, $CaCl_2$ and $MgCl_2$. At high temperatures and/or pressures, water may be hydrolyzed and acids, such as HCl, may form. Corrosion caused by these acids can be economically costly, both in terms of replacement parts and process down-time.

Previously, desalting processes have been used to remove small inorganic salts from crude oil, such as NaCl and $CaCl_2$. These salts are highly soluble, and so they can be removed from crude oil in desalting processes in which only a small amount of water is used. Desalters have not previously been considered useful for removing large organic salts from crude oil.

To date, larger organic molecules, for instance organic acids such as naphthalic acid, have been removed by means of known methods falling within the categories of destruction, adsorption and/or extraction.

Known destruction methods include decarboxylation of the carboxyl group using suitable transition metal catalysts; mixing with calcium oxide; and Statoil's NAR process. Adsorption methods include the use of ion exchange resins; and the use of metal oxides. Extraction methods include the use of polar solvents such as methanol.

Naphthenic acids are carboxylic acids found in crude oil and in various crude oil distillates during the refining of crude oils. The term "naphthenic acids" encompasses a large number of carboxylic acid compounds comprising one or more cycloalkyl rings and having a molecular weight in the range of from about 120 to well over 700. The majority of naphthenic acids found in crude oils and crude oil distillates have a carbon backbone comprising 9 to 20 carbon atoms and cyclopentyl rings are the predominant cycloalkyl ring structure, although other cycloalkyl rings, such as cyclohexyl and cycloheptyl rings may be present in appreciable amounts.

The presence of acidic impurities in crude oil and crude oil distillates causes corrosion of pipelines and distillation equipment at the elevated temperatures used in oil refineries (for example greater than 200° C.), and acidic crude oils and crude oil distillates have reduced market value compared to crude oils and crude oil distillates of low acidity. In particular, distillation of naphthenic acid containing crudes has been found to cause severe corrosion in refinery equipment, especially in vacuum distillation units. Accordingly, effective methods are required to reduce the naphthenic acid content of crude oils and crude oil distillates.

The acidity of crude oils and crude oil distillates is measured in terms of the Total Acid Number (TAN) in accordance with ASTM D0664. The Total Acid Number is the amount of potassium hydroxide in milligrams that is needed to neutralize the acid in one gram of oil, with values in excess of 0.5 mg KOH/g being indicative of high acidity. Typical TAN values for acidic crude oils and crude oil distillates are in the range of 0.5 to 4.0 mg KOH $g^{-1}$, while acidic distillate fractions such as kerosene may have TAN values in the range of, for example, 0.5 to 8.0 mg KOH $g^{-1}$.

WO 2010/136783 relates to a process in which a supported basic ionic liquid is used to neutralise naphthenic acids in crude oil. In such an embodiment, crude oil is passed through a column packed with a supported basic ionic liquid and an oil having a reduced acid content removed from the column.

Ionic liquids are a novel class of compounds which have been developed over the last few years. The term "ionic liquid" as used herein refers to a liquid that is capable of being produced by melting a salt, and when so produced consists solely of ions. An ionic liquid may be formed from a homogeneous substance comprising one species of cation and one species of anion, or it can be composed of more than one species of cation and/or more than one species of anion. Thus, an ionic liquid may be composed of more than one species of cation and one species of anion. An ionic liquid may further be composed of one species of cation, and one or more species of anion. Still further, an ionic liquid may be composed of more than one species of cation and more than one species of anion.

The term "ionic liquid" includes compounds having both high melting points and compounds having low melting points, e.g. at or below room temperature. Thus, many ionic liquids have melting points below 200° C., preferably below 150° C., particularly below 100° C., around room temperature (15 to 30° C.), or even below 0° C. Ionic liquids having melting points below around 30° C. are commonly referred to as "room temperature ionic liquids" and are often derived from organic salts having nitrogen-containing heterocyclic cations, such as imidazolium and pyridinium-based cations. In room temperature ionic liquids, the structures of the cation and anion prevent the formation of an ordered crystalline structure and therefore the salt is liquid at room temperature.

Ionic liquids are most widely known as solvents, because of their negligible vapour pressure, temperature stability, low flammability and recyclability. Due to the vast number of anion/cation combinations that are available it is possible to fine-tune the physical properties of the ionic liquid (e.g. melting point, density, viscosity, and miscibility with water or organic solvents) to suit the requirements of a particular application.

The present invention relates to the surprising discovery that a desalter can be modified in its operation to enable the removal of an ionic liquid and an organic acid from a crude oil.

The present invention provides a process of separating an ionic liquid and an organic acid from a crude oil in a desalting unit, the process comprising the steps of:
  (i) introducing into the desalter a mixture comprising crude oil, ionic liquid and organic acid, together with water in an amount of greater than 10% by volume relative to the mixture; and
  (ii) separating a crude oil phase from one or more liquid phases comprising the ionic liquid, organic acid and water.

Advantageously, the desalting process of the present invention results in the removal of a high proportion of the organic acid from the crude oil mixture. The process of the present invention can remove the organic acid in an amount of greater than 40%, preferably greater than 50%, more preferably greater than 60%, even more preferably greater than 70% and most preferably greater than 80%, by weight as compared to the amount of organic acid in the mixture. For the purposes of the present invention, the term "organic acid" includes salts derived from the organic acid, for instance those salts which may be in the mixture as a result of interactions between the organic acid and the ionic liquid.

Without wishing to be bound by theory, it is believed that the use of water in an amount of greater than 10% by volume relative to the mixture results in the removal of organic acid from crude oil in the form of a temporary oil-in-water emulsion. Without the emulsion, insufficient naphthenate is transferred to the water phase. This is different from the normal operation of a desalter whereby the inorganic salts are entirely dissolved in a small amount of water.

Examples of organic acids that may be present in the crude oil include phenolic acids, sulphur-containing acids, and most commonly, naphthenic acids. Preferably, the organic acid is naphthenic acid.

References to the term crude oil are intended to encompass any crude oil or crude oil distillate. Thus, the process of the present invention may be used with liquefied petroleum gas, gasoline, gas oil, naphtha, kerosene, diesel fuel, fuel oil, jet fuel, home heating oil, lubricating oil or paraffin wax, or mixtures thereof.

Crude oils, such as those referred to above by way of example, are generally processed so as to comprise as little water as possible. This is due to well known issues in both upstream and downstream processes. In this way, in known processes, the amount of water is usually less than 0.5% by volume and preferable less than 0.25% by volume during the extraction of salts from crude oil. The process of the present invention is based upon the surprising finding that it is beneficial to significantly increase the amount of water present. Such increase is generally obtained by way of the addition of water in the amounts defined herein.

The water is preferably contacted with the mixture comprising crude oil, ionic liquid and organic acid in an amount of greater than 15%, preferably greater than 20%, more preferably greater than 25% and most preferably greater than 30% by volume relative to the mixture.

As discussed above, such a high % by volume of water has not previously been used due to known limitations with using high quantities of water in the desalting processes of the prior art. However, the present inventors having surprisingly found that good separations can be obtained when using high concentrations of water.

Moreover, it has surprisingly been found that increasing the % by volume of water, for example from 10% by volume to 30% by volume relative to the mixture, increases the proportion of organic acid which is removed from the mixture. As noted above, it is believed that a high water content results in the formation of an oil-in-water emulsion which enhances the transfer of organic acid, for instance in the form of an organic salt, from the crude oil to the water phase. In contrast, in traditional de-salting processes where as little water as possible is used, the emulsion which forms is a water-in-oil emulsion.

The water is preferably contacted with the mixture in an amount of less than 70%, preferably less than 60%, and more preferably less than 50% by volume relative to the mixture. Amounts of less than 45%, and also less than 40%, by volume are also contemplated.

Thus, by way of example, water may be added in an amount of from greater than 10% to less than 70% by volume relative to the mixture. Within this range, the process of the present invention is effective at removing organic acid, whilst still working efficiently.

In one embodiment, the water may be substantially pure. Thus, the water may comprise impurities/additives in an amount of less than 0.1%, preferably less than 0.05%, more preferably less than 0.01%, and most preferably less than 0.001%, by weight. In other embodiments, the water may comprise one or more additives.

The mixture may be heated prior to being contacted with the water, for example to a temperature in the range of from 60 to 120° C., more preferably from 70 to 110° C., and most preferably from 80 to 100° C. In an embodiment, the temperature is at about 90° C.

The water may be heated prior to being contacted with the mixture, for example to a temperature in the range of from 60 to 100° C., and preferably from 70 to 90° C.

Preferably, both the mixture and the water are heated prior to contact.

Alternatively and/or in addition, heating may occur once the mixture has been contacted with water. Maintaining the mixture at a higher temperature advantageously reduces its viscosity. This eases and speeds up the movement of the mixture through the desalter.

Preferably, a single heated stream is used to heat the mixture and the water, such as by heat exchange. The use of a single heated stream to heat separately both the mixture and the water allows for more efficient heat transfer than, for example, heating the single stream that results from combining the mixture with the water.

Any suitable known systems may be used to heat the streams, and where feasible, it is preferable to heat the streams by way of heat exchange with other heated process streams. By way of example, such a suitable stream may include a heated oil stream. The heated oil stream may be a product stream from the process of the present invention.

It will also be appreciated by those of skill in the art that the ionic liquid may be heated prior to formation of the mixture.

The mixture and the water are preferably subjected to mixing. This results in a temporary emulsion between the mixture and the water, which allows increased movement of the ionic liquid and organic acid from the crude oil to the water. Preferably greater than 50%, preferably greater than 60% and more preferably greater than 70% of the organic acid is transferred to the water phase. Any conditions that may be required for achieving the transfer of the organic acid to the water phase, such as the period of time that mixing is carried out for, can be readily determined by a person of skill in the art.

The mixing may be carried out using any suitable device, for example by passing the mixture and the water through a mixing valve, by using a static mixer or by using a mechanically stirred mixing vessel. Alternatively, mixing may be induced by turbulent flow along a length of pipeline. Preferably, mixing is carried out by passing the mixture and the water through a mixing valve. This allows the mixture and the water to be thoroughly mixed and separated quickly. Excessive mixing of the two phases will give a greater opportunity for the formation of a stable emulsion which is subsequently difficult to separate. The pressure differential across the mixing valve may be, for example, from 1 to 20 psi, more preferably from 4 to 17 psi, and most preferably from 7 to 14 psi.

The mixture is preferably contacted with the water, and preferably mixed (for example by passing through a mixing valve), in a different area from that in which the desalted crude oil phase is separated from the one or more liquid phases comprising the ionic liquid, organic acid and water.

In a preferred embodiment, the mixture is contacted with the water, passed through a mixing valve, and passed to a separating vessel.

Contacting of the mixture with water allows the formation of a deacidified crude oil phase and one or more liquid phases. Preferably, the one or more liquid phases include a water extract phase comprising organic acid and ionic liquid. The desalter preferably comprises a separating vessel in which the phases may form.

Preferably, an electrostatic field is applied in the desalter. This encourages and speeds up the formation of the phases. The electrostatic field may be from 1 to 25 kV, preferably from 1 to 11 kV, more preferably from 3 to 9 kV, and most preferably 5 to 7 kV, alternating current.

The crude oil phase and the one or more liquid phases may be maintained at a temperature of from 60 to 120° C., more preferably from 70 to 110° C., and most preferably from 80 to 100° C. In an embodiment, the temperature is at about 90° C. This is in contrast to normal desalter operations which are typically carried out in a higher temperature range of between 120 and 140° C. A higher temperature enhances the rate of separation, as this results in a lower viscosity of the crude oil, which enhances the rate of oil drainage between coalescing water droplets. There is, however, a trade-off between the benefit of higher temperature and energy expended in raising the temperature of the streams, as well as various other issues such as fouling and higher operating pressures. Usually the balance of various factors leads to a temperature in the abovementioned range of between 120 and 140° C., for instance 130° C. However, in this temperature range there is a risk that the organic salt (formed by reaction of organic acids and ionic liquid) will decompose. Hence, in preferred embodiments of the present invention, the process temperature is limited. It has surprisingly been found that in spite of a lower temperature, the desalting process of the present invention can be effectively used to remove organic acid, such as the larger organic acid naphthenic acid, from crude oil.

Further heating sources, e.g. a heated stream, may be used to maintain the temperature in the desalter. The heated stream is preferably a hot oil stream. In one embodiment, a heated stream is used as a further heating source to maintain the abovementioned temperatures in a separating vessel. In this case, the heated stream preferably passes through the separating vessel in heat exchange contact with the desalted crude oil phase and/or the water extract phase.

The pressure in the desalter is preferably from 100 to 180 psi, more preferably from 120 to 160 psi, and most preferably about 140 psi. Such pressures encourage the lighter fractions of the crude oil and water to remain in the liquid phase.

A number of additives may be used in the process of the present invention. For instance, a demulsifier may be introduced into the desalter to speed up the formation of a desalted crude oil phase and a water extract phase. The use of a demulsifier may also minimise the rag layer. The demulsifier is preferably added before the mixture and the water have been subjected to mixing, and more preferably before the mixture is contacted with the water. This ensures that the demulsifier is able to reach the water and oil interface.

Other additives may be used in the process of the present invention to control emulsions. These additives are also preferably added before the mixture and the water have been subjected to mixing, and more preferably before the mixture is contacted with the water. Suitable additives include pH modifiers, wetting agents and solvents. It is believed that the modification of pH can alter the properties of pH sensitive materials that may stabilise emulsions, by moving them away from the oil/water interface. Wetting agents are surfactants materials capable of coating the surface of solid materials that have a tendency to sit at the interface. By coating the solid particle with surfactant, its solvation properties can be altered and thereby moved away from the interface. The addition of solvents can potentially dissolve certain emulsion stabilising materials such as wax crystals and asphaltenes. They can also lower the viscosity which is believed to increase the rate of film drainage between droplets thereby promoting coalescence. Any method which enhances the rate of separation can be used in the present invention to prevent emulsion stabilising substances from having the opportunity to form a stable emulsion.

Where a demulsifier is used, it may be part of a blend of additives, including for example various types of surfactant, pH modifiers and solvents. The choice of blend may be derived empirically through a series of lab tests, often referred to as 'bottle tests'.

The stability of any emulsion that forms in the process of the present invention may also be minimised by controlling the shear imparted on the crude oil phase and one or more liquid phases.

The deacidified crude oil phase and the one or more liquid phases may be separated in any conventional desalting process. For instance, where the desalted crude oil phase and the one or more liquid phases are in a separating vessel, desalted crude oil may simply be siphoned from the near the top of the separating vessel (the desalted crude oil being, typically, less dense than the one or more liquid phases). A water extract phase comprising organic acid and ionic liquid may be siphoned from near the bottom of the separation vessel.

The process of the present invention may run for greater than 2 hours, preferably for greater than 4 hours, more preferably for greater than 6 hours, still more preferably for greater than 8 hours, and most preferably for greater than 10 hours. A longer run time is preferable as the quantity of ionic liquid and organic acid which is removed from the mixture increases as the conditions in the desalter reach steady state.

In a preferred embodiment, the process of the present invention is a continuous process.

As noted above, for the purposes of the present invention, the term crude oil encompasses any crude oil distillate Thus, the process of the present invention may be used to desalt any liquefied petroleum gas, gasoline, gas oil, naphtha, kerosene, diesel fuel, fuel oil, jet fuel, home heating oil, lubricating oil or paraffin wax, or mixtures thereof.

Preferably, the organic acid containing crude oil has a TAN number of greater than 0.50 mg KOH $g^{-1}$, greater than 1.0 mg KOH $g^{-1}$ or greater than 1.5 mg KOH $g^{-1}$. Examples of organic acids that may be present in the crude oil include phenolic acids, sulphur-containing acids, and most commonly, naphthenic acids. Preferably, the crude oil contains naphthenic acid, and the process of the present invention is for removing naphthenic acid from crude oil. The process of the present invention can result in the extraction of naphthenic acid from the crude oil in an amount of at least 50%, preferably at least 60%, and more preferably at least 70%, by weight as compared to the amount of naphthenic acid in the mixture.

The organic acid containing crude oil is preferably contacted with the ionic liquid in ratio of greater than 50:1, preferably greater than 100:1, and more preferably greater than 125:1, by weight. The organic acid containing crude oil is also preferably contacted with the ionic liquid in ratio of less than 300:1, preferably less than 200:1, and more preferably less than 175:1, by weight. Thus, preferably the organic acid containing crude oil is contacted with the ionic liquid in ratio of from 50:1 to 300:1, preferably from 100:1 to 200:1, and more preferably from 125:1 to 175:1, by weight. In a preferred embodiment, the organic acid containing crude oil is contacted with the ionic liquid in ratio of about 150:1, by weight. It is preferred that the molar amount of basic ionic liquid employed be at least equivalent to, and preferably more than, the molar amount of organic acid in the crude oil and/or crude oil distillate.

The organic acid containing crude oil and the ionic liquid are preferably contacted for a sufficient time to reduce the TAN number of the acid to less than 0.5 mg KOH g$^{-1}$, preferably less than 0.4 mg KOH g$^{-1}$ and more preferably less than 0.3 mg KOH g$^{-1}$. The organic acid containing crude oil and the ionic liquid are preferably mixed. This encourages contact between the organic acid in the crude oil and the ionic liquid, thereby increasing and speeding up the formation of any organic salt. The mixing may be carried out using any of the methods described above, such as those relating to the mixing of the mixture comprising crude oil, ionic liquid and organic acid with water. The time it takes for the acid containing crude oil and ionic liquid to react is highly dependent on how well the acid containing crude oil and ionic liquid are mixed. With vigorous mixing, the reaction is complete within 1 to 5 minutes. Preferably, the mixing process includes passing the organic acid containing crude oil and the ionic liquid through a mixing valve.

The acid containing crude oil and the ionic liquid are preferably heated before being mixed, for example to a temperate of from 60 to 120° C., more preferably from 70 to 110° C., and most preferably from 80 to 100° C. In an embodiment, the temperature is at about 90° C. Typically, the acid containing crude oil and the ionic liquid are mixed at atmospheric pressure.

In an embodiment, the acid containing crude oil may be dehydrated before it is contacted with the ionic liquid. For example, the acid containing crude oil may be dehydrated such that it contains water in an amount of less than 0.5%, preferable less than 0.25%, by volume of oil. Dehydrating the acid containing crude oil before contact with the ionic liquid increases the rate at which organic salt forms, particularly when the ionic liquid is water soluble. The water may be separated from the acid containing crude oil in, for example, a coalescer.

In addition to organic acids, the process of the present invention may be used to remove inorganic salts from the acid containing crude oil.

Preferably, this may be done during the process described above, with both the organic acids and inorganic salts being removed.

However, it will be appreciated that the processes of the present invention may be used in conjunction with known de-salting processes. By way of example, inorganic salts may be removed from the acid containing crude oil in a pre-treatment step using a conventional desalting process. In such a conventional process, the desalter is usually operated at a temperature of between 120 and 140° C., preferably 130° C. and/or the water content in the desalter is usually less than 5% by volume of oil, preferably less than 1% by volume of oil. Such processes are known to those of skill in the art.

Once pre-treated, the acid containing crude oil is passed to a process in accordance with the present invention. As described above, this process involves introducing into the desalter a mixture comprising crude oil, ionic liquid and organic acid, together with water in an amount of greater than 10% by volume relative to the mixture. The desalting unit is preferably maintained at a temperature of from 60 to 120° C., for instance of about 90° C.

In addition or alternatively to the pre-treatment above, the process may further comprise a 'post-treatment' step in which any inorganic salts are separated from the treated acid containing crude oil by way of separation.

The ionic liquid which is used in the process of the present invention is preferably a basic ionic liquid.

The basic ionic liquid may be one in which the anion is basic, the cation is basic or the anion and the cation are both basic. Preferably, the anion is basic or the anion and the cation are both basic.

Preferably, the ionic liquid used in the present invention has a basic anion selected from serinate, prolinate, histidinate, threoninate, valinate, asparaginate, taurinate, lysinate, alkylcarbonate and hydrogen carbonate.

In a preferred embodiment of the present invention, the basic anion is selected from serinate, lysinate, prolinate, taurinate and threoninate, more preferably from lysinate, prolinate and serinate. The basic anion may also be selected from histidinate and taurinate.

In another preferred embodiment, the basic anion is an alkylcarbonate. More preferably the alkyl group may be linear or branched, and/or may additionally be substituted or unsubstituted.

In one preferred embodiment the alkyl group is unsubstituted. In another preferred embodiment the alkyl group is unbranched. In a more preferred embodiment the alkyl group is unsubstituted and unbranched.

In the embodiments of the present invention, the alkyl group may comprise from 1 to 30 carbon atoms, preferably from 1 to 20 carbon atoms and more preferably form 1 to 10 carbon atoms.

The alkyl groups may be selected from one or more of methyl, ethyl, propyl, butyl, pentyl, hexyl, heptyl, octyl, nonyl and/or decyl. Especially preferred are methyl, ethyl, propyl, butyl and pentyl. In a further preferred embodiment the alkyl groups are selected from methyl and ethyl.

It will be understood that branched alkyl groups such as iso-propyl, iso-butyl, sec-butyl and/or tert-butyl may also be used.

The basic ionic liquid may comprise a cation selected or derived from the group consisting of: ammonium, azaannulenium, azathiazolium, benzimidazolium, benzofuranium, benzothiophenium, benzotriazolium, borolium, cinnolinium, diazabicyclodecenium, diazabicyclononenium, diazabicycloundecenium, dibenzofuranium, dibenzothiophenium, dithiazolium, furanium, guanidinium, imidazolium, indazolium, indolinium, indolium, morpholinium, oxaborolium, oxaphospholium, oxathiazolium, oxazinium, oxazolium, iso-oxazolium, oxazolinium, pentazolium, phospholium, phosphonium, phthalazinium, piperazinium, piperidinium, pyranium, pyrazinium, pyrazolium, pyridazinium, pyridinium, pyrimidinium, pyrrolidinium, pyrrolium, quinazolinium, quinolinium, iso-quinolinium, quinoxalinium, selenazolium, sulfonium, tetrazolium, thiadiazolium, iso-thiadiazolium, thiazinium, thiazolium, iso-thiazolium, thiophenium, thiuronium, triazadecenium, triazinium, triazolium, iso-triazolium, and uronium.

In one embodiment, the cation may be selected from the group consisting of:

wherein: $R^a$, $R^b$, $R^c$, $R^d$, $R^e$, $R^f$ and $R^g$ are each independently selected from hydrogen, a $C_1$ to $C_{30}$, straight chain or branched alkyl group, a $C_3$ to $C_8$ cycloalkyl group, or a $C_6$ to $C_{10}$ aryl group, wherein said alkyl, cycloalkyl or aryl groups are unsubstituted or may be substituted by one to three groups selected from: $C_1$ to $C_6$ alkoxy, $C_2$ to $C_{12}$ alkoxyalkoxy, $C_3$ to $C_8$ cycloalkyl, $C_6$ to $C_{10}$ aryl, —CN, —OH, —SH, —NO$_2$, $C_6$ to $C_{10}$ aryl and $C_7$ to $C_{10}$ alkaryl, —CO$_2$($C_1$ to $C_6$)alkyl, —OC(O)($C_1$ to $C_6$)alkyl, or any two of $R^b$, $R^c$, $R^d$, $R^e$ and $R^f$ attached to adjacent carbon atoms form a methylene chain —(CH$_2$)$_q$— wherein q is from 3 to 6.

Preferably, $R^a$, $R^b$, $R^c$, $R^d$, $R^e$, $R^f$ and $R^g$ are each independently selected from a $C_1$ to $C_{20}$ straight chain or branched alkyl group, a $C_3$ to $C_6$ cycloalkyl group, or a $C_6$ aryl group, wherein said alkyl, cycloalkyl or aryl groups are unsubstituted or may be substituted by one to three groups selected from: $C_1$ to $C_6$ alkoxy, $C_2$ to $C_{12}$ alkoxyalkoxy, $C_3$ to $C_8$ cycloalkyl, $C_6$ to $C_{10}$ aryl, —CN, —OH, —SH, —NO$_2$, —CO$_2$($C_1$ to $C_6$)alkyl, —OC(O) ($C_1$ to $C_6$)alkyl, $C_6$ to $C_{10}$ aryl and $C_7$ to $C_{10}$ alkaryl, and wherein one of $R^b$, $R^c$, $R^d$, $R^e$, $R^f$ and $R^g$ may also be hydrogen.

$R^a$ is preferably selected from $C_1$ to $C_{30}$, linear or branched, alkyl, more preferably $C_2$ to $C_{20}$ linear or branched alkyl, still more preferably, $C_2$ to $C_{10}$ linear or branched alkyl, and most preferably $R^a$ is selected from ethyl, n-butyl, n-hexyl and n-octyl. Further examples include wherein $R^a$ is selected from methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl and n-octadecyl.

In the cations comprising an $R^g$ group, $R^g$ is preferably selected from $C_1$ to $C_{10}$ linear or branched alkyl, more preferably, $C_1$ to $C_5$ linear or branched alkyl, and most preferably $R^g$ is a methyl group.

In the cations comprising both an $R^a$ and an $R^g$ group, $R^a$ and $R^g$ are each preferably independently selected from $C_1$ to $C_{30}$, linear or branched, alkyl, and one of $R^a$ and $R^g$ may also be hydrogen. More preferably, one of $R^a$ and $R^g$ may be selected from $C_2$ to $C_{20}$ linear or branched alkyl, still more preferably, $C_2$ to $C_{10}$ linear or branched alkyl, and most preferably $C_4$ to $C_8$ linear or branched alkyl, and the other one of $R^a$ and $R^g$ may be selected from $C_1$ to $C_{10}$ linear or branched alkyl, more preferably, $C_1$ to $C_5$ linear or branched alkyl, and most preferably a methyl group. In a further preferred embodiment, $R^a$ and $R^g$ may each be independently selected, where present, from $C_1$ to $C_{30}$ linear or branched alkyl and $C_1$ to $C_{15}$ alkoxyalkyl.

In another embodiment, the cation may be selected from the group consisting of:

$[N(R^a)(R^b)(R^c)(R^d)]^+$, $[P(R^a)(R^b)(R^c)(R^d)]^+$, and $[S(R^a)(R^b)(R^c)]^+$, wherein: $R^a$, $R^b$, $R^c$ and $R^d$ are as defined above.

Preferably, the cation is selected from:

$[N(R^a)(R^b)(R^c)(R^d)]^+$, wherein: $R^a$, $R^b$, $R^c$ and $R^d$ are each independently selected from $C_1$ to $C_8$ alkyl, including $C_2$, $C_4$ and $C_6$ alkyl.

In a preferred embodiment, $R^a$ is methyl. For instance, $R^a$ may be methyl and $R^b$, $R^c$ and $R^d$ may be independently selected from $C_2$ to $C_6$ alkyl, including $C_2$, $C_4$ and $C_6$ alkyl. Preferred cations include tributyl(methyl)ammonium and triethyl(methyl)ammonium.

The basic ionic liquid may comprise a basic cation represented by the formula:

Cat$^+$-(Z-Bas)$_n$ wherein: Cat$^+$ is a positively charged moiety;
Bas is a basic moiety;
Z is a covalent bond joining Cat$^+$ and Bas, or is a divalent linking group; and
n is an integer of from 1 to 3, and preferably n is 1.

Suitably, Bas comprises at least one basic nitrogen, phosphorus, sulfur, or oxygen atom, preferably, at least one basic nitrogen atom.

Bas may comprise a heterocyclic ring system containing a basic nitrogen atom, such as a pyrrolidine or piperidine ring.

Preferably, Bas is selected from —N(R$^1$)(R$^2$), —P(R$^1$) (R$^2$) and —SR$^3$. Bas may also be —OR$^3$. Suitably, R$^1$ and R$^2$ are independently selected from hydrogen, linear or branched alkyl, cycloalkyl, aryl and substituted aryl, or, in the case of an —N(R$^1$)(R$^2$) group, R$^1$ and R$^2$ together with the interjacent nitrogen atom form part of a heterocyclic ring. Suitably, R$^3$ is selected from linear or branched alkyl, cycloalkyl, aryl and substituted aryl.

Preferably, $R^1$, $R^2$ and $R^3$ are selected from methyl, ethyl, n-propyl, isopropyl, n-butyl, isobutyl, tert-butyl, n-pentyl, n-hexyl, cyclohexyl, benzyl and phenyl, or, in the case of an —N($R^1$)($R^2$) group, $R^1$ and $R^2$ together represent a tetramethylene or pentamethylene group optionally substituted by one or more $C_{1-4}$ alkyl groups.

In one embodiment, the basic moiety is a "hindered basic group" i.e. is a functional group that acts as a base and, owing to steric hindrance, does not chemically bond to any of the components of the oil (other of course than by accepting a proton in the usual reaction of a Brønsted acid with a Brønsted base). Suitable hindered basic groups include —N(CH($CH_3$)$_2$)$_2$ and —N(C($CH_3$)$_3$)$_2$. Preferably, the hindered basic group has a lower nucleophilicity (or greater steric hindrance) than —N($C_2H_5$)$_3$.

In the context of the present invention, the group —OH is not considered basic due to difficulties with protonation. Accordingly, Bas as defined herein does not include —OH, and in a preferred embodiment, does not include —$OR^3$.

Z may be a divalent organic radical having from 1 to 18 carbon atoms, preferably 1 to 8 carbon atoms, more preferably, 2 to 6 carbon atoms. The divalent organic radical, Z, may be branched or unbranched. The divalent organic radical, Z, may be substituted or unsubstituted. Preferably, the valence bonds are on different carbon atoms of the divalent organic radical, Z.

Suitably, the divalent organic radical, Z, is a divalent aliphatic radical (for example, alkylene, alkenylene, cycloalkylene, oxyalkylene, oxyalkyleneoxy, alkyleneoxyalkylene or a polyoxyalkylene) or is a divalent aromatic radical (for example, arylene, alkylenearylene or alkylenearylenealkylene).

Preferably, Z is:
(a) a divalent alkylene radical selected from: —($CH_2$—$CH_2$)—, ($CH_2$—$CH_2$—$CH_2$)—, —($CH_2$—$CH_2$—$CH_2$—$CH_2$)—, —($CH_2$—$CH_2$—$CH_2$—$CH_2$—$CH_2$)—, —($CH_2$—$CH_2$—$CH_2$—$CH_2$—$CH_2$—$CH_2$)—, —($CH_2$—CH($CH_3$))—, and —($CH_2$—CH($CH_3$)—$CH_2$—CH($CH_3$))—;
(b) a divalent alkyleneoxyalkylene radical selected from: —($CH_2$—$CH_2$—O—$CH_2$—$CH_2$)—, —($CH_2$—$CH_2$—O—$CH_2$—$CH_2$—O—$CH_2$—$CH_2$)—, and —($CH_2$—CH($CH_3$)—O—$CH_2$—CH($CH_3$))—
(c) a divalent polyoxyethylene radical selected from: —($CH_2CH_2O$)$_n$— where n is an integer in the range 1 to 9 or —($CH_2CH(CH_3)O$)$_m$— where m is an integer in the range 1 to 6; and
(d) a divalent alkylenearylene or an alkylenearylenealkylene radical selected from: —($CH_2$—$C_6H_4$)—, and —($CH_2$—$C_6H_4$—$CH_2$)—.

The Cat$^+$ moiety may comprise a heterocyclic ring structure selected from: ammonium, azaannulenium, azathiazolium, benzimidazolium, benzofuranium, benzothiophenium, benzotriazolium, borolium, cinnolinium, diazabicyclodecenium, diazabicyclononenium, diazabicycloundecenium, dibenzofuranium, dibenzothiophenium, dithiazolium, furanium, guanidinium, imidazolium, indazolium, indolinium, indolium, morpholinium, oxaborolium, oxaphospholium, oxathiazolium, oxazinium, oxazolium, iso-oxazolium, oxazolinium, pentazolium, phospholium, phosphonium, phthalazinium, piperazinium, piperidinium, pyranium, pyrazinium, pyrazolium, pyridazinium, pyridinium, pyrimidinium, pyrrolidinium, pyrrolium, quinazolinium, quinolinium, iso-quinolinium, quinoxalinium, selenazolium, sulfonium, tetrazolium, thiadiazolium, iso-thiadiazolium, thiazinium, thiazolium, iso-thiazolium, thiophenium, thiuronium, triazadecenium, triazinium, triazolium, iso-triazolium, and uronium.

Examples of Cat$^+$-Z-Bas where Cat$^+$ is a heterocyclic ring structure include:

wherein: Bas and Z are as defined above; and $R^b$, $R^c$, $R^d$, $R^e$, $R^f$ and $R^g$ are independently selected from hydrogen, a $C_1$ to $C_{40}$, straight chain or branched alkyl group, a $C_3$ to $C_8$ cycloalkyl group, or a $C_6$ to $C_{10}$ aryl group, wherein said alkyl, cycloalkyl or aryl groups are unsubstituted or may be substituted by one to three groups selected from: $C_1$ to $C_6$ alkoxy, $C_6$ to $C_{10}$ aryl, CN, OH, $NO_2$, $C_7$ to $C_{30}$ aralkyl and $C_7$ to $C_{30}$ alkaryl, or any two of $R^b$, $R^c$, $R^d$, $R^e$ and $R^f$ attached to adjacent carbon atoms on the ring structure form a methylene chain —(CH$_2$)$_p$— wherein p is an integer from 3 to 5.

Preferred Cat$^+$-Z-Bas, where Cat$^+$ is a heterocyclic ring structure, includes:

wherein: Bas, Z and R$^b$ are as defined above.

It is particularly preferred that Cat$^+$ is a heterocyclic ring structure and Bas is a sterically hindered amino group, for example:

The heterocyclic Cat$^+$ moiety may be obtained by alkylation, protonation and/or acylation of a precursor selected from: azaannulenes, azathiazoles, benzimidazoles, benzofurans, benzothiophenes, benzotriazoles, boroles, cinnolines, diazabicyclodecenes, diazabicyclononenes, diazabicycloundecenes, dibenzofurans, benzothiophenes, dibenzothiophenes, dithiazoles, furans, imidazoles, indazoles, indolines, indoles, morpholines, oxaboroles, oxaphospholes, oxathiazoles, oxazines, oxazoles, iso-oxazoles, oxazolines, pentazoles, phospholes, phthalazines, piperazines, piperidines, pyrans, pyrazines, pyrazoles, pyridazines, pyridines, pyrimidines, pyrrolidines, pyrroles, quinazolines, quinolines, iso-quinolines, quinoxalines, selenazoles, tetrazoles, thiadiazoles, iso-thiadiazoles, thiazines, thiazoles, isothiazoles, thiophenes, triazadecenes, triazines, triazoles, iso-triazoles.

It is also envisaged that the Cat$^+$ moiety may be an acyclic hydrocarbyl moiety. Preferably, the acyclic hydrocarbyl moiety comprises a group selected from amino amidino, imino, guanidino, phosphino, arsino, stibino, alkoxyalkyl, alkylthio, alkylseleno and phosphinimino.

Where the Cat$^+$ moiety is an acyclic hydrocarbyl moiety, [Cat$^+$-Z-Bas] is preferably selected from:

wherein: Bas, Z, R$^b$, R$^c$, and R$^d$ are as defined above. It is particularly preferred that R$^b$, R$^c$, and R$^d$ are independently selected from methyl and ethyl.

Examples of preferred [Cat$^+$-Z-Bas] of this class include:

where Bas is the sterically hindered amino group, —N(CH(CH$_3$)$_2$)$_2$.

[Cat$^+$-Z-Bas] may also be:

wherein: R$^b$ is as defined above.

Preferred ionic liquids for use in the process of the present invention include triethyl(methyl)ammonium methyl carbonate and tributyl(methyl)ammonium methyl carbonate. Amino acid based ionic liquids are also preferred. Particularly preferred is tributyl(methyl)ammonium methyl carbonate.

In a preferred embodiment, the ionic liquid is water soluble. For instance, the ionic liquid may be soluble in water in an amount of greater than 1%, preferably greater than 5%, more preferably greater than 10%, and most preferably greater than 20%, by weight in water.

Where the ionic liquid is water soluble, it may be recovered in an amount of greater than 30%, preferably more than 40%, more preferably greater than 60%, and still more preferably greater than 70%, by weight of the ionic liquid introduced into the desalting unit.

In an embodiment, the ionic liquid is miscible with the crude oil. For instance, the ionic liquid may be soluble in the oil phase at a concentration of greater than 50 ppm, preferably greater than 500 ppm, and more preferably greater than 5000 ppm. However, to ensure separation of the crude oil phase from the one or more liquid phases comprising the ionic liquid, organic acid and water, it is important that both those salts which may be in the mixture as a result of interactions between the organic acid and the ionic liquid and any residual unreacted ionic liquid are able to preferentially transfer to the one or more aqueous phases.

Where the one or more liquid phases include a water extract phase comprising organic acid and ionic liquid, the process of the present invention may additionally comprise the step of separating the ionic liquid and the organic acid. This is preferably by way of a process in which the ionic liquid is regenerated, and preferably by way of a process in which both the ionic liquid and the organic acid are regenerated.

Suitable regeneration methods include:
(1) extraction of the organic acids into a solvent that is immiscible with the ionic liquid;
(2) vaporization of the acids at a reduced pressure and at a temperature less than the decomposition temperature of the ionic liquid, preferably, a temperature less than 200° C.;
(3) gas stripping wherein a hot gas, for example steam or nitrogen is passed through the ionic liquid to volatilize the acids;
(4) extraction of the acids with a supercritical fluid, for example, liquefied carbon dioxide;
(5) membrane separation (polymer-based, ceramic, zeolite and liquid-liquid systems) where the membrane is selectively permeable to the acids; and
(6) a combination of two or more of the above methods.

Where the ionic liquid is a basic ionic liquid, the regeneration process preferably comprises (i) contacting the basic ionic liquid with an acid having a pKa of less than 6.75; and, optionally, (ii) contacting the mixture of step (i) with a solvent which is immiscible with the basic ionic liquid; and (iii) separating the solvent from the ionic liquid. Using this method, the ionic liquid may be regenerated in an amount of greater than 80%, preferably greater than 90%, and more preferably greater than 95%, as compared to the amount ionic liquid added to the crude oil in the process. Preferably, the acid is carbonic acid. Also preferably, the solvent is naphtha. For example, where an alkyl ammonium ionic liquid is contacted with a naphthenic acid containing crude oil, a mixture will form which includes alkyl ammonium naphthenate salt. Contacting the mixture with carbonic acid results in the ionic liquid and the naphthenic acid reforming. Addition of naphtha enhances the efficiency of the regeneration.

In one preferred method of regeneration, the organic acids contained in the water extract phase are reacted with a Group 1 and/or Group 2 metal hydroxide (for example calcium hydroxide) such that at least a portion of the acids, preferably, substantially all of the acids, are converted into Group 1 and/or Group 2 neutralization salts thereof within the ionic liquid. For example, the water extract phase may be contacted with solid Group 1 and/or Group 2 metal hydroxide. Without wishing to be bound by any theory, it is believed that the neutralization salts formed by the reaction of the Brønsted acid and the Brønsted base may precipitate from the ionic liquid and may therefore be readily separated therefrom.

The Group 1 metal hydroxide may be selected from lithium hydroxide, sodium hydroxide, and potassium hydroxide, preferably, sodium hydroxide. Suitably, the Group 2 metal hydroxide is selected from barium hydroxide, magnesium hydroxide, and calcium hydroxide, preferably, calcium hydroxide. Mixtures of Group 1 and/or Group 2 metal hydroxides may be employed. However, it is preferred to employ a Group 2 metal salt or mixtures thereof owing to the risk of Group 1 metal salts of the acids forming soaps that can interfere with the separation of water from the basic ionic liquid. Particularly preferred is calcium hydroxide.

In a further preferred method, the organic acids contained in the water extract phase are reacted with a Group 1 and/or Group 2 metal carbonate salt (for example Dolomite—$CaMg(CO_3)_2$), such that at least a portion of the acids, preferably, substantially all of the acids, are converted into Group 1 and/or Group 2 neutralization salts thereof. Where the carbonate salt is a solid, the ionic liquid phase of reduced organic acid content may be recovered by filtration.

The water extract phase may be contacted with a brine, for example, seawater or a produced water, on a production platform where the pH of the seawater is adjusted using a base to a value of at least 8, preferably at least 10 during the contacting step. Seawater contains naturally occurring Group 1 and Group 2 metal ions in an amount sufficient to complex with the acids contained in the basic ionic liquid. Typically, the pH of the brine may be adjusted to a value in the range 10 to 12 so that the pH of the brine after neutralization of the acids is in the range 4 to 9. The pH of the seawater may be adjusted using a Group 1 and/or 2 metal hydroxide, for example, sodium hydroxide.

It is also envisaged that the water extract phase may be contacted with a $C_1$ to $C_6$ aliphatic alcohol in the presence of an esterification catalyst (for example, a heterogeneous or homogeneous esterification catalyst) under conditions effective to convert at least a portion of the acids into the corresponding esters thereof. These ester derivatives are more volatile than the acids and hence are more readily separated from the basic ionic liquid, for example, by vaporization at reduced pressure and at a temperature of less than 150° C.

The deacidified crude oil which is obtained in step (ii) of the process of the present invention may be used directly for other purposes or may be further processed, for example, by fractional distillation. If necessary, any residual ionic liquid that remains may be recovered by passing the product oil stream through a silica column such that the ionic liquid is adsorbed onto the silica column. The adsorbed basic ionic liquid may then be washed off the silica column using a solvent for the ionic liquid and the ionic liquid may be recovered by driving off the solvent at reduced pressure. Alternatively, the oil may be removed from the residual ionic liquid by hot gas stripping using, for example, hot nitrogen gas.

The present invention will now be described, by way of example only, with reference to the accompanying Figures, in which.

Figure 1:
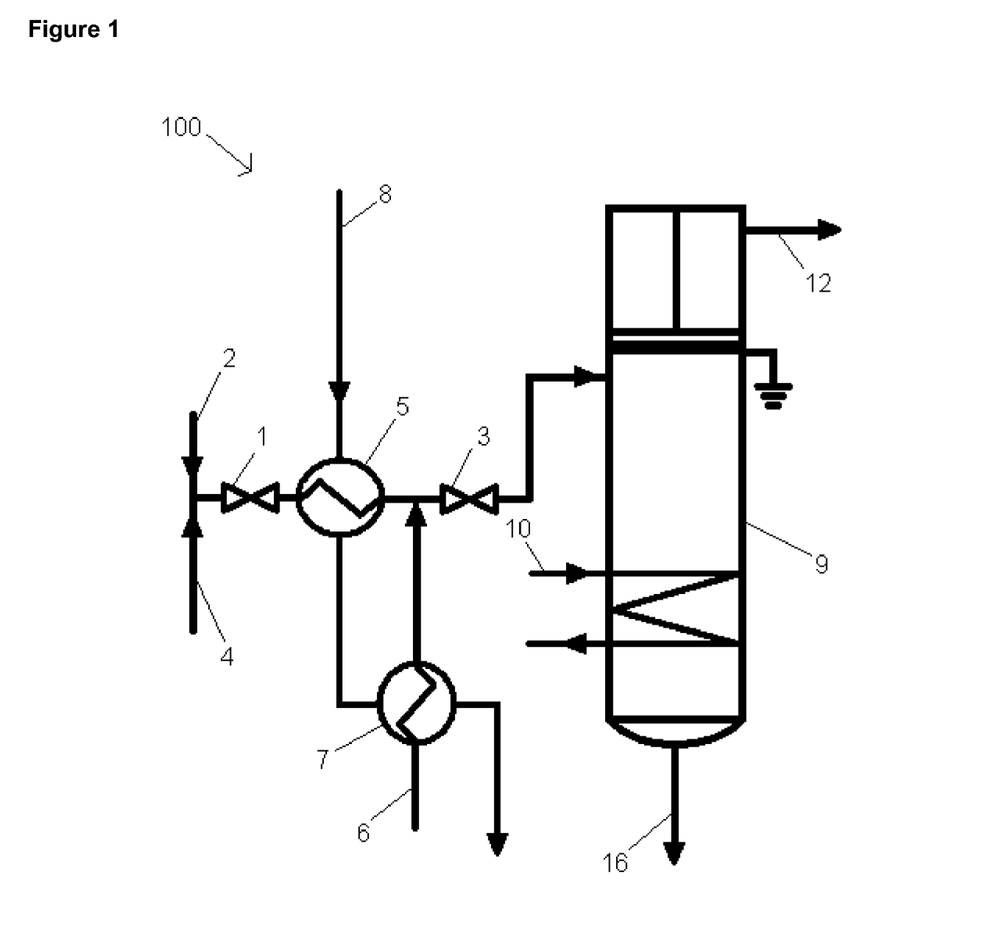
FIG. 1 shows a process flow diagram of a process in accordance with the present invention.

Looking at FIG. 1, there is shown a desalter 100 which has been adapted for carrying out the process of the present invention. In the desalter 100, a stream 2 comprising of crude oil and organic acid is contacted with an ionic liquid feed stream 4 to form a mixture comprising crude oil, organic acid and ionic liquid. This mixture is passed through a first mixing valve 1 and then through a first heat exchanger 5. The mixture is heated in the first heat exchanger 5 (preferably to a temperature in the range of 80 to 100° C.) in heat exchange with a first hot oil stream 8.

A water feed stream 6 is heated by way of a second heat exchanger 7. The water feed stream 6 is heated in the second heat exchanger 7 (preferably to a temperature of 70 to 90° C.) in heat exchange with the first hot oil stream 8.

In the embodiment shown in FIG. 1, it can be seen that the first hot oil stream 8 passes in heat exchange contact with the mixture comprising crude oil, organic acid and ionic liquid, and subsequently with the water feed stream 6. Accordingly, the heating imparted to the feed water stream 6 is less than that imparted to the mixture stream.

The heated water feed stream exiting the second heat exchanger 7 is contacted with the heated mixture comprising crude oil, organic acid and ionic liquid. Once contacted, the resulting combination is passed through a further mixing valve 3 and into a separating vessel 9.

The temperature in the separator vessel 9 is maintained at 90° C. by means of heat exchange with a second hot oil stream 10. An electrostatic field is applied to increase the rate of separation.

A deacidified crude oil phase is formed in the separating vessel 9 and extracted as a product stream 12, with an aqueous phase comprising organic acid and ionic liquid being formed as a by-product and extracted as stream 16.

The deacidified crude oil phase 12, being less dense than the aqueous phase 16, is extracted near the top of the separator vessel.

The present inventions will now be described further by way of example.

EXAMPLES

The examples were carried out using a vertical desalter manufactured by Howe Baker Engineers (Serial No.: 1498; Year built: 1980). The separating vessel of the desalter was maintained at a temperature of about 90° C.

The crude oil used in the examples is from an Australian field and is called Pyrenees. The crude oil has a TAN of 1.5 mg KOH g$^{-1}$. The crude oil was subjected to constant circulation before use so as to prevent stratification.

The ionic liquid used in the examples is tributyl(methyl) ammonium methyl carbonate. The ionic liquid was added in 0.7 wt % concentration with respect to the crude.

As the naphthenate anion forms an association with the tributyl(methyl)ammonium cation, the quantity of naphthenate salt which is extracted from the crude oil is based upon the quantity of tributyl(methyl)ammonium cation which is extracted, as measured using NMR. Unlike naphthenate anions which vary in structure, tributyl(methyl)ammonium cations give a clear set of peaks on an NMR spectrum.

Example 1

Use of Water in an Amount of 10% by Volume of Mixture

Acidic crude oil was mixed with ionic liquid in an amount of 0.7% by weight of acidic crude oil until the TAN of the crude oil was measured to be <0.3 mg KOH g$^{-1}$ of oil. Mixing was achieved by passing the stream through a mixing valve and was complete within 4 hours.

The salt containing crude oil was then combined with an aqueous stream in a continuous mode of operation to form a mixture containing approximately 10% water by volume. Further mixing was achieved by passing the combined streams through a second mixing valve.

The stream was then fed into a separating vessel containing an electrostatic field of 6 kV alternating current which increased the rate of phase separation.

Figure 3:
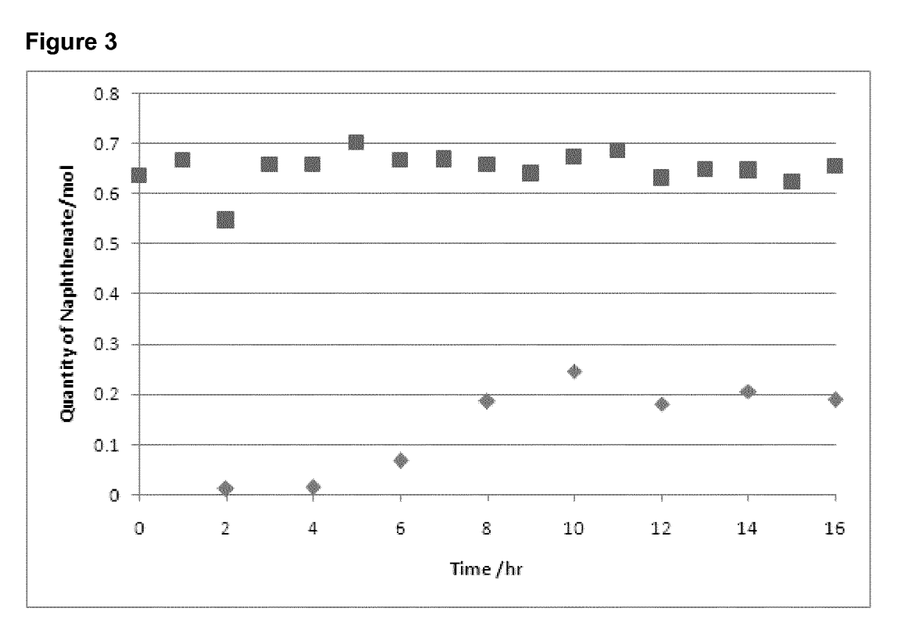
FIG. 3 is a graph showing the quantity of naphthenate salt extracted (diamonds) from, and the quantity of naphthenate salt in the feed (squares) to, a process which utilises water in an amount of 10% by volume of the mixture, as a function of process operating time.

The process was analyzed to determine the amount of naphthenate salt that was recovered from the process. The quantity of naphthenate salt that was recovered increased as the process approaches steady state conditions. It can be seen from FIG. 3 that, once the process had reached steady state conditions, the recovery of the naphthenate salt was greater than 30 mol %.

Example 2

Use of Water in an Amount of 30% by Volume of Mixture

Figure 2:
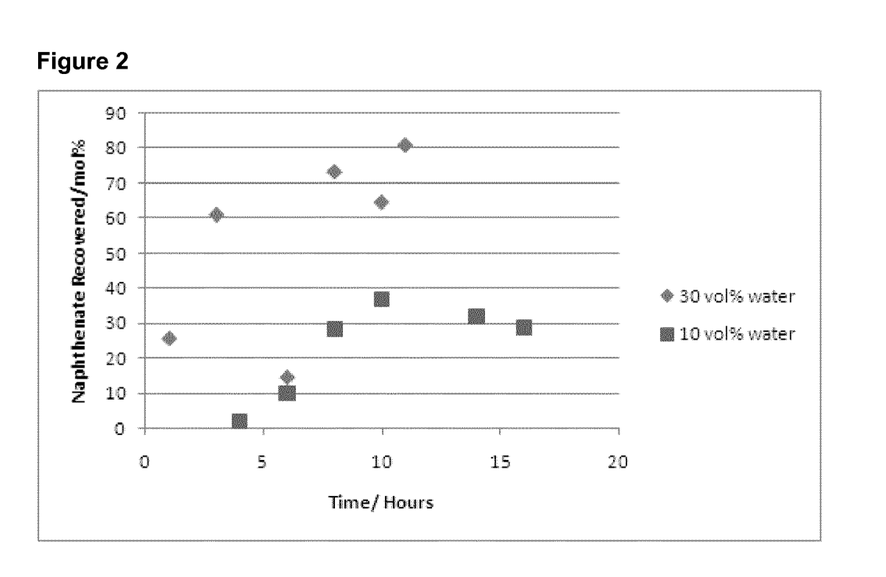
FIG. 2 is a graph comparing the quantity of naphthenate salt extracted from a process which utilises water in an amount of 10% and of 30% by volume of the mixture, as a function of process operating time.

By utilizing an identical set-up as in Example 1, but increasing the water feed to an amount of 30% water by volume of mixture, the total quantity of recoverable naphthenate salt can be increased to greater than 70 mol % (see FIG. 2).

Figure 4:
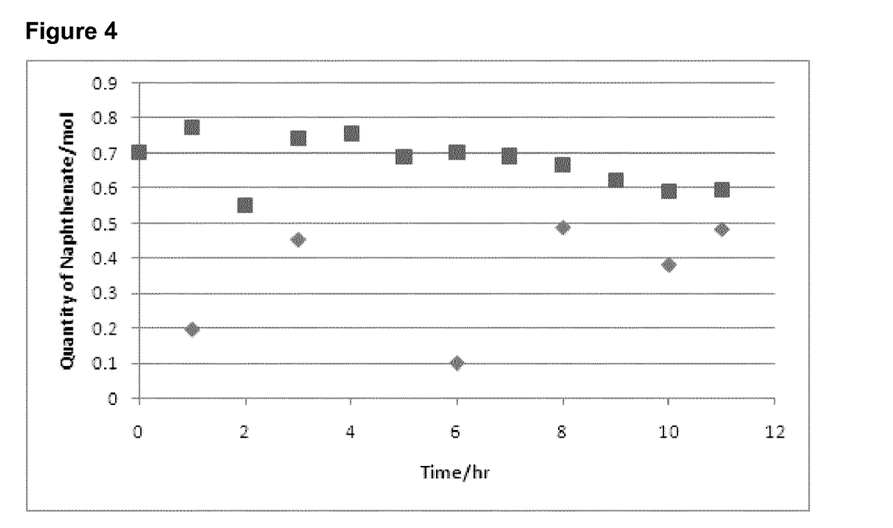
FIG. 4 is a graph showing the quantity of naphthenate salt extracted (diamonds) from, and the quantity of naphthenate salt in the feed (squares) to, a process which utilises water in an amount of 30% by volume of the mixture, as a function of process operating time.
Figure 5:
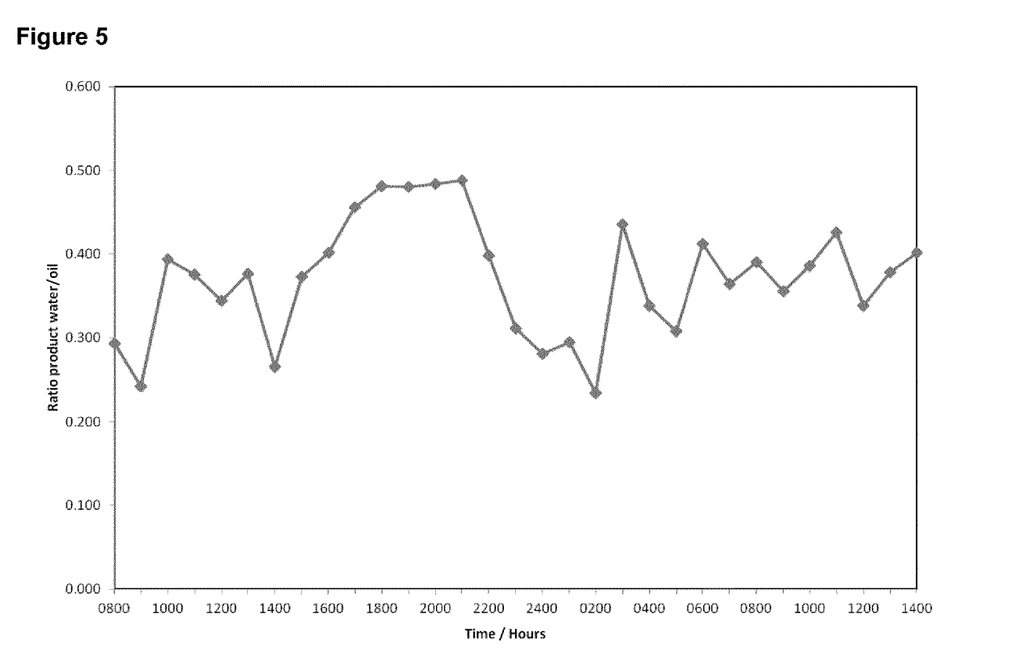
FIG. 5 is a graph showing the ratio of product water to product crude oil from a process in which water is used in an amount of 30% by volume of the mixture, as a function of process operating time.
Figure 6:
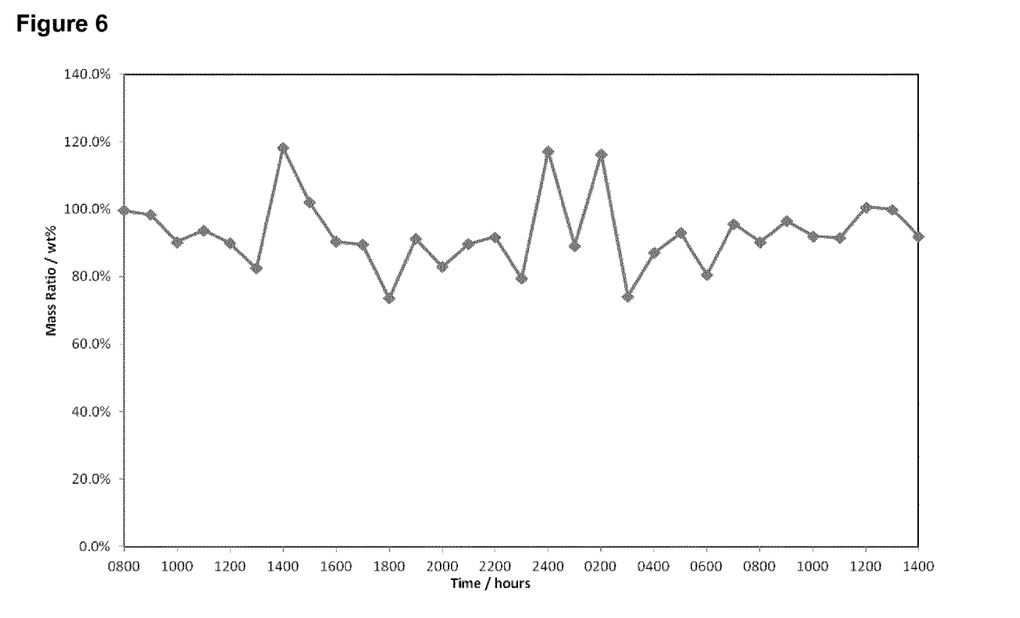
FIG. 6 is a graph showing crude oil mass balance from a process in which water is used in an amount of 30% by volume of the mixture, as a function of process operating time.
Figure 7:
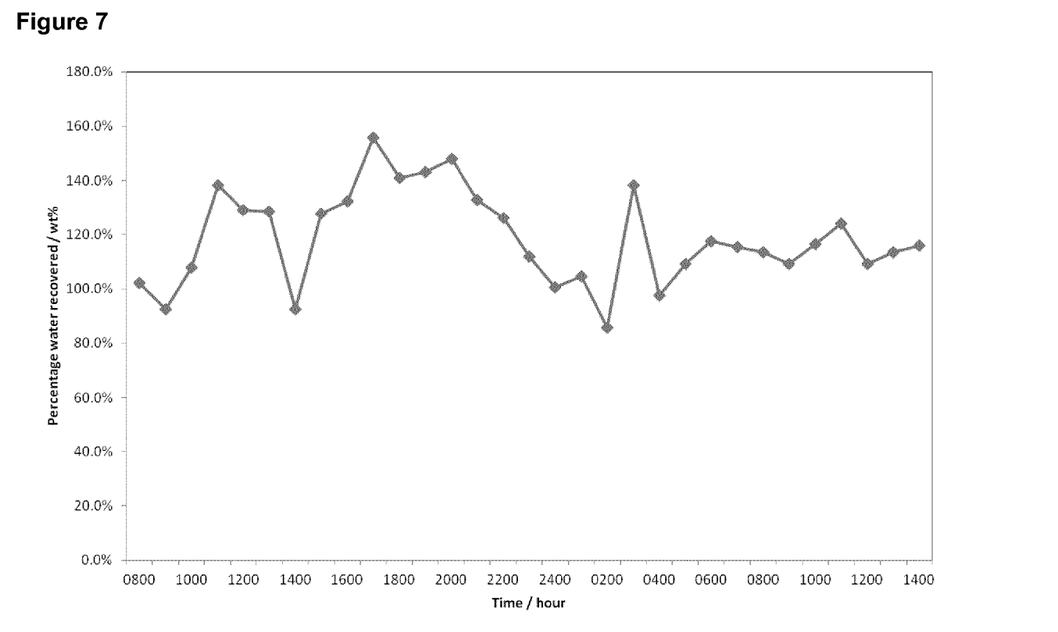
FIG. 7 is a graph showing water mass balance from a process in which water is used in an amount of 30% by volume of the mixture, as a function of process operating time.
Figure 8:
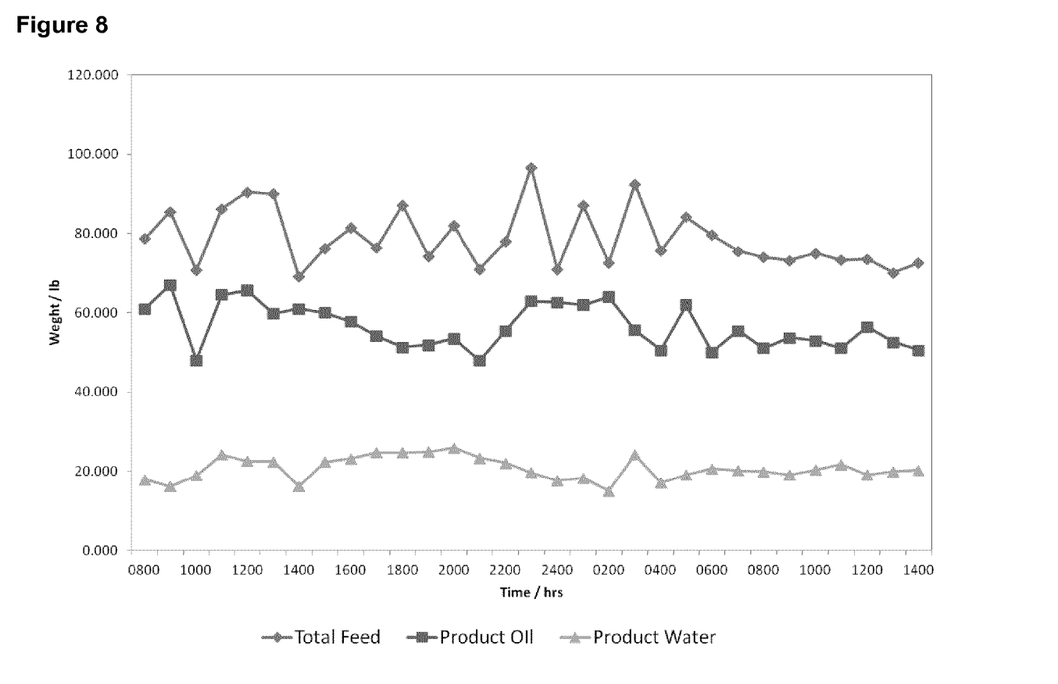
FIG. 8 is a graph showing the amount of total feed to a process in which water is used in an amount of 30% by volume of the mixture, as well as the amounts of crude oil product and water product from the process, as a function of process operating time.
Figure 9:
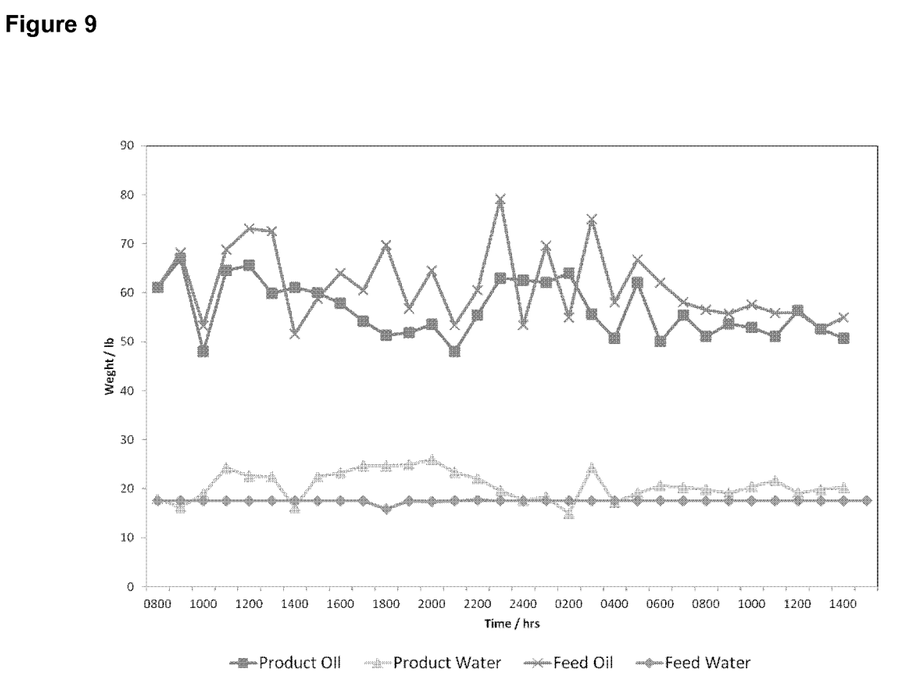
FIG. 9 is a graph showing the amounts of feed mixture and feed water to a process in which water is used in an amount of 30% by volume of the mixture, as well as the amounts of crude oil product and water product from the process, as a function of process operating time.

It can be seen from FIG. 4 that, once the process had reached steady state conditions, the recovery of the naphthenate salt was greater than 30 mol %.

This demonstrates that by increasing the amount of water added to the process, the recovery of the naphthenate salt from the mixture is improved.

FIGS. 5 to 9 also show mass balance data from a process in which water is used in an amount of 30% by volume of the mixture.

The invention claimed is:

1. A process of separating an ionic liquid from a crude oil and an organic acid from the crude oil in a desalter, the process comprising the steps of:
   (i) introducing into the desalter a mixture comprising crude oil, an ionic liquid, and an organic acid, together with water in an amount of greater than 30% by volume relative to the mixture; and
   (ii) separating a crude oil phase from one or more liquid phases comprising the ionic liquid, organic acid, and water.

2. The process of claim 1, wherein the water is introduced into the desalter in an amount of less than 70% by volume relative to the mixture.

3. The process of claim 1, wherein the mixture and the water are subjected to mixing.

4. The process of claim 3, wherein the mixture and the water are passed through a mixing valve.

5. The process of claim 4, wherein the pressure differential across the mixing valve is from 1 psi to 20 psi.

6. The process of claim 1, wherein an electrostatic field is applied to the desalter.

7. The process of claim 6, wherein the electrostatic field is from 1 kV AC to 25 kV AC.

8. The process of claim 1, wherein the desalter is maintained at a temperature of from 60° C. to 120° C.

9. The process of claim 1, wherein a demulsifier is introduced into the desalter.

10. The process of claim 1, wherein the one or more liquid phases include a water extract phase comprising the organic acid and the ionic liquid and the process further comprises the step of separating the ionic liquid and the organic acid.

11. The process of claim 10, wherein at least one of the ionic liquid and the organic acid are regenerated.

12. The process of claim 1, wherein the organic acid is naphthenic acid.

13. The process of claim 1, wherein the process is a continuous process.

14. The process of claim 1, wherein the ionic liquid is a basic ionic liquid.

15. The process of claim 14, wherein the ionic liquid comprises a basic anion selected from at least one member of a group consisting of: serinate, prolinate, histidinate, threoninate, valinate, asparaginate, taurinate, lysinate, alkylcarbonate and hydrogen carbonate.

16. The process of claim 15, wherein the basic anion is an alkylcarbonate.

17. The process of claim 14, wherein the basic ionic liquid comprises a cation selected or derived from the group consisting of: ammonium, azaannulenium, azathiazolium, benzimidazolium, benzofuranium, benzothiophenium, benzotriazolium, borolium, cinnolinium, diazabicyclodecenium, diazabicyclononenium, diazabicycloundecenium, dibenzofuranium, dibenzothiophenium, dithiazolium, furanium, guanidinium, imidazolium, indazolium, indolinium, indolium, morpholinium, oxaborolium, oxaphospholium, oxathiazolium, oxazinium, oxazolium, iso-oxazolium, oxazolinium, pentazolium, phospholium, phosphonium, phthalazinium, piperazinium, piperidinium, pyranium, pyrazinium, pyrazolium, pyridazinium, pyridinium, pyrimidinium, pyrrolidinium, pyrrolium, quinazolinium, quinolinium, iso-quinolinium, quinoxalinium, selenazolium, sulfonium, tetrazolium, thiadiazolium, iso-thiadiazolium, thiazinium, thiazolium, iso-thiazolium, thiophenium, thiuronium, triazadecenium, triazinium, triazolium, iso-triazolium, and uronium.

18. The process of claim 17, wherein the cation is selected from the group consisting of:

wherein: $R^a$, $R^b$, $R^c$, $R^d$, $R^e$, $R^f$ and $R^g$ are each independently selected from hydrogen, a $C_1$ to $C_{30}$, straight chain or branched alkyl group, a $C_3$ to $C_8$ cycloalkyl group, or a $C_6$ to $C_{10}$ aryl group, wherein said alkyl, cycloalkyl or aryl groups are unsubstituted or may be substituted by one to three groups selected from: $C_1$ to $C_6$ alkoxy, $C_2$ to $C_{12}$ alkoxyalkoxy, $C_3$ to $C_8$ cycloalkyl, $C_6$ to $C_{10}$ aryl, —CN, —OH, —SH, —NO$_2$, $C_6$ to $C_{10}$ aryl and $C_7$ to $C_{10}$ alkaryl, —CO$_2$($C_1$ to $C_6$)alkyl, —OC(O)($C_1$ to $C_6$)alkyl, or any two of $R^b$, $R^c$, $R^d$, $R^e$ and $R^f$ attached to adjacent carbon atoms form a methylene chain —(CH$_2$)$_q$— wherein q is from 3 to 6.

19. The process of claim 17, wherein the cation is selected from:

wherein: $R^a$, $R^b$, $R^c$ and $R^d$ are as defined in claim 18.

20. The process of claim 19, wherein the cation is selected from:

, wherein: $R^a$, $R^b$, $R^c$ and $R^d$ are each independently selected from $C_1$ to $C_8$ alkyl, including $C_2$, $C_4$ and $C_6$ alkyl.

21. The process of claim 20, wherein the cation is tributyl(methyl)ammonium or triethyl(methyl)ammonium.

22. The process of claim 14, wherein the basic ionic liquid comprises a cation represented by the formula:

wherein: $Cat^+$ is a positively charged moiety;
Bas is a basic moiety;
Z is a covalent bond joining $Cat^+$ and Bas, or is a divalent linking group; and
n is an integer of from 1 to 3.

23. The process of claim 22, wherein [$Cat^+$-Z-Bas] is selected from the group consisting of:

24. A process according to claim 1, wherein the acid containing crude oil is pre-treated in a de-salter to remove inorganic salts.

* * * * *